United States Patent [19]
Schatz et al.

[11] Patent Number: 5,273,527
[45] Date of Patent: Dec. 28, 1993

[54] DELIVERY CATHETER

[75] Inventors: Richard A. Schatz, Rancho Santa Fe; John N. Zink, Mountain View, both of Calif.; Robert S. Schenken, San Antonio, Tex.; Brian M. Packard, Monticello; Jon Kagan, Minneapolis, both of Minn.

[73] Assignee: Ovamed Corporation, Palo Alto, Calif.

[21] Appl. No.: 881,778

[22] Filed: May 12, 1992

[51] Int. Cl.$^5$ ............................................. A61M 25/00
[52] U.S. Cl. ........................................ 604/43; 604/164; 604/280
[58] Field of Search .................. 604/27, 35, 36, 38, 604/43, 45, 55, 164, 170, 264, 280, 906; 600/33-35; 128/656, 658

[56] References Cited

U.S. PATENT DOCUMENTS

| | | | |
|---|---|---|---|
| 883,583 | 3/1908 | Stallsmith | 604/43 |
| 1,060,665 | 5/1913 | Bell . | |
| 2,574,840 | 11/1951 | Pieri et al. | 128/349 |
| 2,688,329 | 9/1954 | Wallace | 128/349 |
| 3,421,509 | 1/1969 | Fiore | 128/349 |
| 3,467,101 | 9/1969 | Fogarty et al. | 128/348 |
| 3,605,725 | 9/1971 | Bentov | 128/2.05 R |
| 3,636,940 | 1/1972 | Gravlee | 604/38 |
| 3,968,800 | 7/1976 | Vilasi | 128/343 |
| 4,033,331 | 7/1977 | Guss et al. | 128/2 M |
| 4,195,637 | 4/1980 | Grüntzig et al. | 128/348 |
| 4,307,722 | 12/1981 | Evans | 128/344 |
| 4,323,071 | 4/1982 | Simpson et al. | 128/343 |
| 4,324,262 | 4/1982 | Hall | 128/756 |
| 4,325,387 | 4/1982 | Helfer | 128/748 |
| 4,502,482 | 3/1985 | Deluccia et al. | 128/207.15 |
| 4,545,390 | 10/1985 | Leary | 128/772 |
| 4,571,240 | 2/1986 | Samson et al. | 604/96 |
| 4,586,923 | 5/1986 | Gould et al. | 604/95 |
| 4,596,564 | 6/1986 | Spetzler et al. | 604/45 |
| 4,650,467 | 3/1987 | Bonello et al. | 604/95 |
| 4,655,214 | 4/1987 | Linder | 128/207.18 |
| 4,808,155 | 2/1989 | Mahurkar | 604/43 |
| 5,021,044 | 6/1991 | Sharkawy | 604/53 |
| 5,108,366 | 4/1992 | Schatz | 604/55 |
| 5,167,623 | 12/1992 | Cianci et al. | 604/43 |

Primary Examiner—John D. Yasko
Assistant Examiner—Anthony Gutowski
Attorney, Agent, or Firm—Nydegger & Associates

[57] ABSTRACT

A delivery catheter for introducing living matter into a body passageway or cavity of a female mammal comprises a hollow, flexible, dual lumen catheter having substantially tubular-shaped collection chamber for holding the living matter. An ejection port is formed adjacent to the distal end of the collection chamber and an actuator port is formed at its proximal end. A guide tube having a lumen, is positioned coaxially within the collection chamber with the respective distal and proximal ends of the guide tube and the collection chamber joined together in fluid-tight sealing engagements. In an alternate embodiment, the lumina are separated to create a guide wire lumen which is substantially parallel to a transfer lumen. Also, the distal end of the catheter is beveled to recess the opening of the guide wire lumen from the port of the collection chamber in the transfer lumen. In operation, the delivery catheter is inserted into the body passageway over a prepositioned guide wire. More specifically, the delivery catheter receives the guide wire through the lumen of its guide tube to advance the delivery catheter along the guide wire. Once the ejection port of the collection chamber is positioned at the desired site in the body passageway, fluid is introduced into the collection chamber through the actuator port to eject the living matter through the ejection port and into the body passageway. The delivery catheter and the guide wire are then withdrawn from the passageway.

12 Claims, 4 Drawing Sheets

DELIVERY CATHETER

FIELD OF THE INVENTION

The present invention generally pertains to devices for introducing matter into a body cavity. More specifically, the present invention pertains to delivery catheters which can be guided through body passageways to deposit living matter or medication at a desired location in the passageway. The present invention is particularly, but not exclusively, useful for depositing fertilized eggs or gametes in the fallopian tubes of a female mammal to initiate gestation.

BACKGROUND OF THE INVENTION

It is well-known that infertility is a subject which has been of great interest and concern within the medical community. This is so, in part, because it is known that infertility may result for several reasons. For example, the male and female gametes may have different antibodies which prevent fertilization. Further, it may happen that the male has a low sperm count or that the female gamete is not capable of being fertilized. There may also be mechanical factors involved. For instance, if the fallopian tubes of the female have been impaired by a disorder or have been somehow blocked, such as by a tubal ligation, it will be necessary to deposit a fertilized egg directly into the uterus, rather than the fallopian tube, before there can be any possibility of gestation.

Numerous procedures have been suggested to accomplish the intrafallopian transfer of zygotes or gametes. One of the more widely used and well-known medical procedures is laparoscopy. For laparoscopy, the fertilized egg is implanted in the distal third portion of the fallopian tube via a surgical procedure which requires an incision in the abdominal wall of the female. A syringe-like device is then inserted through the incision to deposit a fertilized egg at the desired site within the fallopian tube. Laparoscopy, however, is a surgical operation with potential complications. For example, if the required surgical incision is not properly closed, the healing process may be unnecessarily prolonged. Moreover, as with any surgical procedure requiring operative incisions, a mandatory recuperation period in the hospital is required. Also, as with other surgical procedures requiring operative incisions, there is relatively a greater risk of infection than with medical procedures that do not require operative incisions.

It is known, however, that access into body passageways need not necessarily require surgical operative incisions and, instead, may be accomplished using catheters. Indeed, catheter technology has developed markedly in several areas of medical technology. Specifically, catheters are frequently used in cardiology. As an example, for transluminal coronary angioplasty, catheters are inserted into the cardiovascular system in order to remodel a blockage or obstruction in the artery. Indeed, such a catheter is disclosed and claimed in U.S. Pat. No. 4,571,240 to Samson et al. for an invention entitled "Catheter Having Encapsulated Tip Marker". In accordance with the Samson et al. disclosure, a catheter is inserted into the coronary artery over a prepositioned guide wire until an inflatable balloon is positioned across the lesion to be compromised. In another application, U.S. Pat. No. 3,968,800, which issued to Vilasi for an invention entitled "Device for Insertion into a Body Opening" discloses a catheter-like device which is an essentially hollow tube which is useful as endotracheal tubes, bronchoscope, vascular and cervical dilators and the like. Although these and other devices are exemplary of catheters and their varied uses, none of these devices are intended to deal with the problems associated with infertility. Further, they do not suggest the use of a catheter for depositing living matter into a body passageway for subsequent gestation. Importantly, the present invention recognizes a catheter can be used for delivering zygotes into the fallopian tubes of a female mammal without requiring operative incisions.

For the specific application wherein the catheter is to be used for the transfer of biological samples, living tissue, or pharmaceutical compositions into the fallopian tube of a female, there are additional factors to be addressed which deserve special consideration. First, there is the need to keep the catheter as small as possible. This is particularly important when a guide wire is to be used for proper insertion and positioning of the catheter in a fallopian tube. Second, in view of the miniaturization requirement, there is also a need to facilitate positioning of the distal end of the catheter with matter to be transferred. Alignment of the catheter with the matter is necessary for aspiration of the matter into the collection chamber of the transfer catheter. And third, the smallness of a dual lumen catheter establishes a need to minimize the possibility that undesired capillary action may inadvertently draw the matter to be transferred into the guide wire lumen rather than into the collection chamber of the transfer lumen.

In light of the above, it is an object of the present invention to provide a catheter for introducing living matter into a body passageway. Another object of the present invention is to provide a delivery catheter that can accomplish intrafallopian transfer of zygotes on an outpatient basis. Still another object of the present invention is to provide a catheter which can accomplish intrafallopian transfer of zygotes through direct access of the catheter to the fallopian tube through a body orifice. Another object of the present invention is to provide a transfer catheter which allows the port of its collection chamber to be positioned in a manner which facilitates the aspiration of matter into the collection chamber of the catheter. Still another object of the present invention is to provide a delivery catheter which reduces fluid friction forces in the transfer lumen of the catheter during aspiration and expulsion of matter from the collection chamber and which minimizes unwanted capillary action into the guide wire lumen of the catheter during aspiration. Yet another object of the present invention is to provide a delivery catheter that is relatively easy to operate, relatively simple to manufacture and comparatively cost-effective for its intended purposes.

SUMMARY OF THE INVENTION

A delivery catheter is provided to initiate gestation by introducing living matter, such as zygotes or gametes, into the fallopian tubes of a female mammal. Additionally, the delivery catheter can be used to aspirate biological material from the fallopian tubes of a mammal to provide a natural culture media in which to fertilize eggs. In accordance with the present invention, such a delivery catheter comprises a hollow, flexible elongated guide tube which is formed with a lumen. A tubular-shaped collection chamber having a wall is disposed as a sheath in a surrounding relationship to the guide tube. In this surrounding relationship, the distal and proximal ends of the collection chamber are joined in respective fluid-tight seals with the distal and proximal ends of the guide tube. An ejection port is formed in the wall of the collection chamber adjacent to its distal end and an actuator port is formed in the wall of the collection chamber at its proximal end. The actuator port is engageable with a syringe or other fluid-injecting device to introduce fluid into the collection chamber.

In operation, a guide wire is initially positioned through a body orifice and into the desired body passageway; for example, through the vagina and cervix, and into the fallopian tube. Before insertion of the delivery catheter into the body passageway, the delivery catheter is primed by filling the collection chamber with fluid. Zygotes are then collected in the collection chamber and held therein near the ejection port. For insertion of the delivery catheter into the body passageway, the prepositioned guide wire is slidably received into the lumen of the guide tube and the guide tube and its associated collection chamber are then advanced along the guide wire. Once the ejection port of the collection chamber is positioned at the desired site in the body passageway, ejection of the living matter (i.e. the zygotes), or medication, from the collection chamber is accomplished by introducing fluid into the collection chamber through the actuator port.

In an alternate embodiment of the present invention, the guide tube is eliminated and, instead, a guide lumen is formed into the sidewall of the collection chamber. Specifically, for this embodiment of the present invention, the collection chamber is still configured as a tubular-shaped member. The distal end of the collection chamber, however, is now either left open to form the ejection port, or is closed if the ejection port is to be formed into the wall of the collection chamber. Further, a guide lumen is formed into a sidewall of the collection chamber with one opening of the guide lumen located at the distal end of the collection chamber and the other opening of the guide lumen located on the sidewall of the collection chamber. The guide lumen is dimensioned to receive the guide wire and, in the operation of this embodiment, the guide lumen is surroundingly engaged over the guide wire to advance the collection chamber along a prepositioned guide wire.

Another alternate embodiment of a delivery catheter in accordance with the present invention comprises a hollow, flexible tubular-shaped collection chamber for holding the matter to be introduced. The distal end and the proximal end of this collection chamber are closed. For this embodiment of the delivery catheter, as with the preferred embodiment, an ejection port is formed at the distal end of the collection chamber and an actuator port, which is engageable with a syringe or other fluid injecting device, is formed at the proximal end of the collection chamber. A guide catheter having a lumen for receiving the collection chamber is concentrically positionable around the collection chamber.

For still another embodiment of the delivery/transfer catheter of the present invention, the catheter is a dual lumen catheter which includes a guide wire lumen substantially parallel with a transfer lumen. The transfer lumen has a collection chamber with a port which is formed in fluid communication with the collection chamber at the distal end of the catheter body. The guide wire lumen has an opening at the distal end of the catheter body which is beveled relative to the port of the collection chamber. This effectively recesses the opening of the guide wire lumen from the port of the transfer lumen. The transfer catheter of this embodiment can also have an opaque distal end to facilitate visual positioning of the distal end when aspirating matter into the collection chamber. The portion of the distal end which is opaque need not be excessive and, indeed, should be sufficiently small to allow the user of the transfer catheter to be able to view the biological material held in the collection chamber. Alternatively, the transfer catheter can have a translucent or a transparent distal end for this same purpose. Further, all embodiments of the present invention can include a syringe type device connectable at the proximal end of the transfer lumen to draw matter into the chamber through the port of the collection chamber and to subsequently expel the matter therefrom.

For the manufacture of the dual lumen embodiment of the transfer catheter according to the present invention, several definitive steps are required. First, an elongated catheter body having a distal end and a proximal end is extruded with two lumina. One lumen is the guide wire lumen and it has a substantially circular cross section for receiving a guide wire. The other lumen is a transfer lumen and it is extruded to initially have a substantially crescent shaped cross section. Next, a pin is inserted into the distal end of the crescent shaped transfer lumen and subsequently withdrawn to simultaneously create a substantially cylindrical shaped collection chamber and a port into the collection chamber at the tip of the distal end of the catheter body. Finally, with the pin removed, the distal end of the catheter body is beveled across the circular shaped guide wire lumen to effectively recess its opening from the port of the collection chamber. Additionally, a connector can be attached to the proximal end of the transfer lumen for attaching an aspirating device, such as a syringe, in fluid communication with the transfer lumen to aspirate matter into the collection chamber and to subsequently expel the matter from the collection chamber.

In the operation of this embodiment, the guide catheter is initially positioned through the vagina and into the fallopian tube. The zygote-filled collection chamber is then slidably received into the lumen of the guide catheter and the collection chamber is advanced along the guide catheter. Once the ejection port of the collection chamber is positioned at the desired site within the fallopian tube, ejection of the living matter is accomplished by introducing fluid into the collection chamber through the actuator port.

Operation of the present invention also contemplates the aspiration of biological material from the fallopian tube of a mammal to provide a natural culture media in which to fertilize eggs. To accomplish this task, the guide wire or guide catheter is inserted into the fallopian tube and the transfer catheter is subsequently positioned along the guide wire or guide catheter with its distal end at a desired location in the fallopian tube. Material is then aspirated from the fallopian tube into the collection chamber and the transfer catheter is withdrawn. With the transfer catheter withdrawn from the fallopian tube, the collected material can then be discharged from the collection chamber and used as desired.

The novel feature of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENTS

Figure 1:
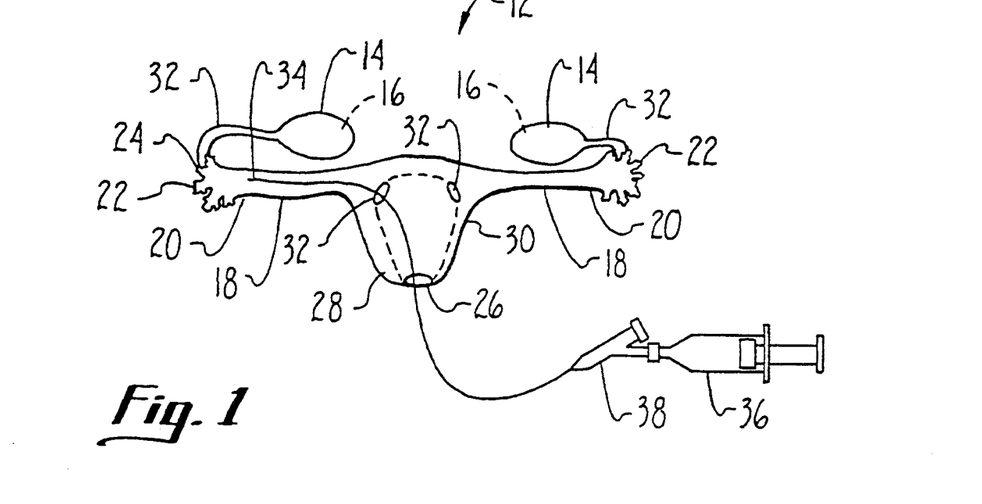
FIG. 1 is a schematic showing the present invention operatively positioned through a body passageway.

Referring initially to FIG. 1, a delivery catheter according to the present invention is generally designated 10 and is shown operatively positioned in a female reproductive system 12.

The portions of the female reproductive system 12 shown in FIG. 1 include the ovaries 14 in which ova 16 are produced, the fallopian tubes 18 in which fertilization is normally accomplished, and the cervix 28 through which sperm must pass en route to their destiny with the ova in the fallopian tube 18. Under normal conditions of fertilization, ova 16 are conveyed from the ovary 14 to the distal third portion 20 of fallopian tube 18 by ciliated motion via the fimbria 22 and fimbria ovarica 24.

As shown in FIG. 1, delivery catheter 10 is positioned through the os externium 26 of cervix 28 through the uterus 30 and through the os 32 into the fallopian tube 18. When properly positioned, the distal end 34 of delivery catheter 10 is located in the distal third portion 20 of fallopian tube 18. FIG. 1 also shows a syringe 36 engaged with actuator port 38.

Figures 2, 5:
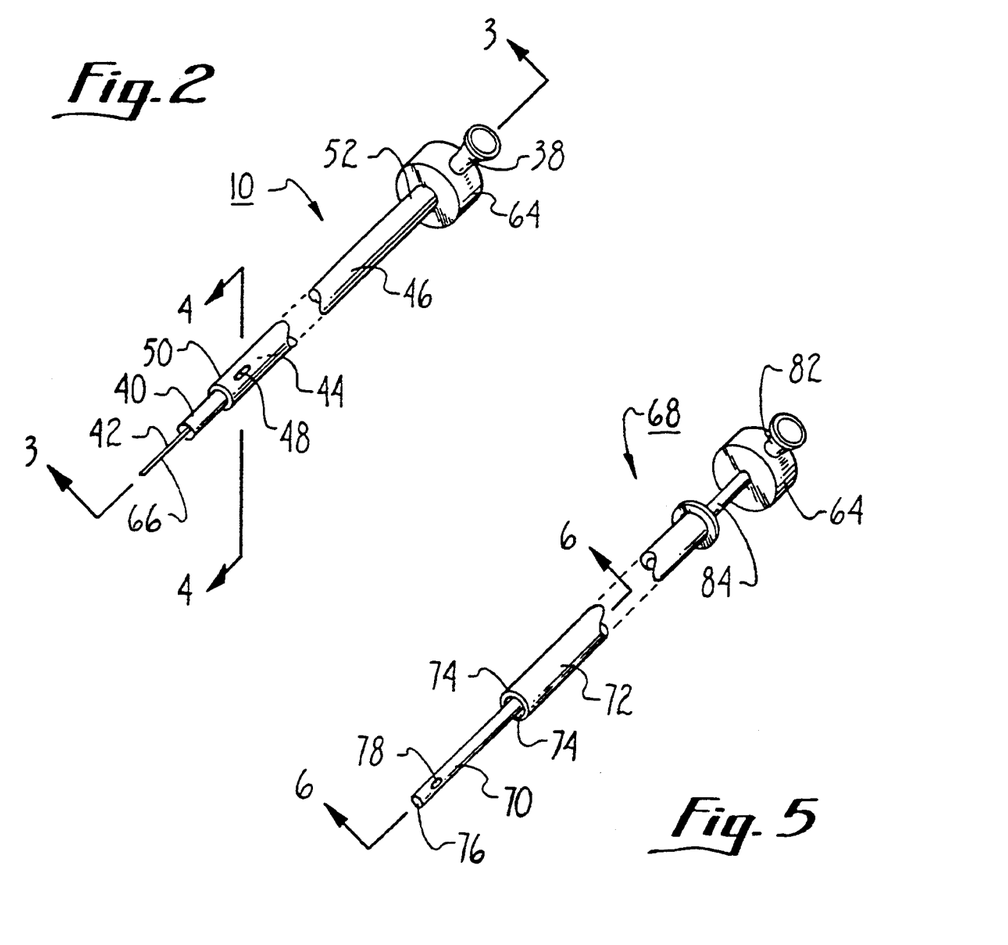
FIG. 2 is a perspective view of the preferred embodiment of the delivery catheter according to the present invention.
FIG. 5 is a perspective view of an alternate embodiment of the delivery catheter according to the present invention.

Referring now to FIG. 2, it will be seen that the delivery catheter 10 comprises an elongated, flexible guide tube 40 which is formed with a lumen 42. As shown, guide tube 40 is concentrically positioned inside a tubular-shaped collection chamber 44 which is disposed as a sheath 46 in a surrounding relationship to guide tube 40. Further, it can be seen in FIG. 2 that collection chamber 44 is formed with an ejection port 48 near its distal end 50 and with an actuator port 38 near its proximal end 52. As perhaps better appreciated with reference to FIG. 3, the proximal end 52 and distal end 50 of the collection chamber 44 are joined in respective fluid-tight seals 54 with the proximal end 58 and distal end 56 of guide tube 40. For purposes of the present invention, the fluid-tight seals 54, are made in any manner well-known in the pertinent art such as by gluing or solvent bonding.

Figure 3:
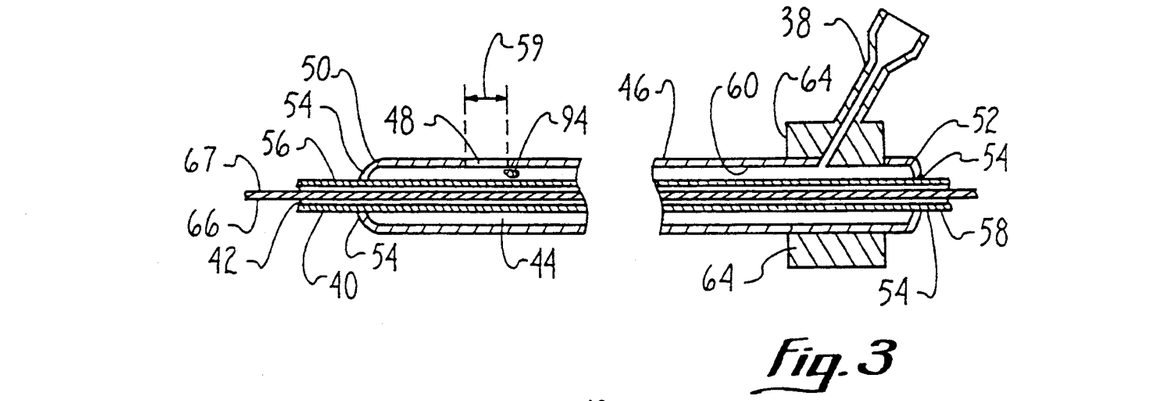
FIG. 3 is a cross-sectional view of the catheter as seen along the line 3—3 in FIG. 2.
Figure 4:
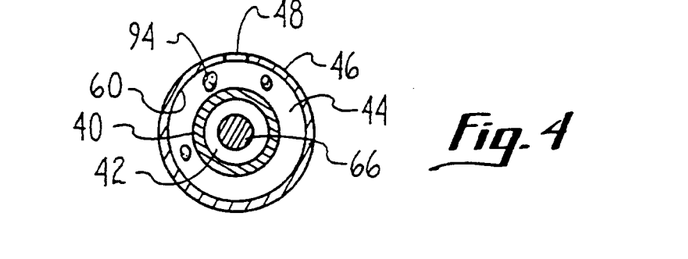
FIG. 4 is a cross-sectional view of the catheter as seen along the line 4—4 in FIG. 2.

As will be seen in cross-reference between FIGS. 2 and 3, the ejection port 48 is formed in the wall 60 of collection chamber 44 adjacent to its distal end 50. Preferably, ejection port 48 is sufficiently large enough to allow living matter to be safely ejected from delivery catheter 10. Preferably, ejection port 48 is circular and has a diameter 59 of approximately one half millimeter (0.5 mm). The actuator port 38 is also formed in the wall 60 of collection chamber 44 and, although shown in FIGS. 2 and 3 as being located adjacent or near the proximal end 52 of the collection chamber 44, the actuator port 38 can be formed anywhere along wall 60 of collection chamber 44 in accordance with the desires of the operator. In any event, actuator port 38 has a fitting 64 which extends from the wall 60 of collection chamber 44 for engagement with a syringe 36 or other fluid-injecting device. FIGS. 2, 3 and 4 also show that guide wire 66 is slidably received through the lumen 42 of guide tube 40. For purposes of the present invention, guide wire 66 may be any steerable or positionable guide wire that is well-known in the pertinent art. Importantly, guide wire 66 must be capable of being properly positioned in the body passageway and is biologically compatible with the body.

Figure 6:
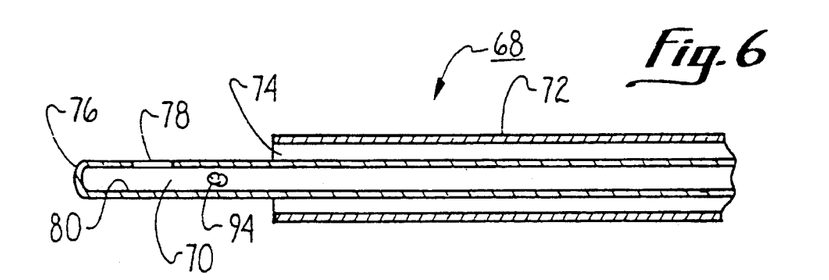
FIG. 6 is a cross-sectional view of a portion of the catheter as seen along the line 6—6 in FIG. 5.

In an alternate embodiment of the present invention, as shown in FIG. 5, a delivery catheter, generally designated 68, comprises a hollow, flexible tubular-shaped collection chamber 70 which can be inserted through the lumen 74 of a guide catheter 72. More specifically, and as perhaps best seen in FIG. 6, the distal end 76 of collection chamber 70 is closed and has an ejection port 78 formed in wall 80 of collection chamber adjacent to this distal end 76. For this embodiment, an actuator port 82, shown in FIG. 5, is formed in wall 80 at the proximal end 84 of collection chamber 70 which is engageable with a syringe 36 or other fluid-injecting device for purposes to be subsequently discussed in conjunction with the operation of the present invention. As can be appreciated by reference to FIG. 6, delivery catheter 68 is insertable through the lumen 74 of a guide catheter 72. Moreover, like guide wire 66, guide catheter 72 is steerable or positionable into a body passageway.

Figure 7:
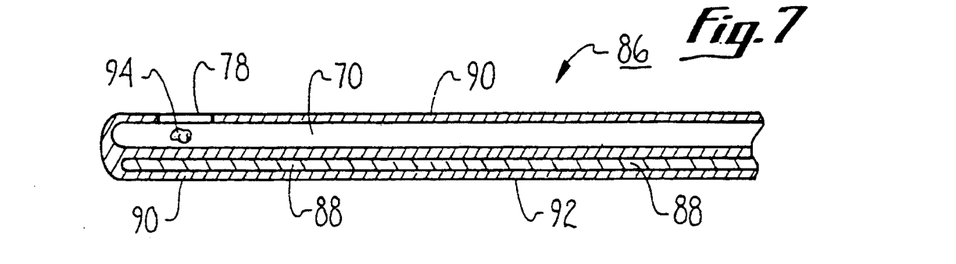
FIG. 7 is a cross-sectional view of a portion of the catheter shown in FIG. 5 with a flexible guide member.

As seen in FIG. 7, a delivery catheter, generally designated 86, can include a flexible steering member 88 which is embedded within the wall 90 of collection chamber 70. More specifically, steering member 88 can be used and manipulated in a manner similar to that of guide wire 66. Thus, with a member 88 incorporated as part of collection chamber 70, the collection chamber 70 can, itself, be positioned in the body passageway without using the positioning capability of either a guide wire 66 or a guide catheter 72.

Figure 8:
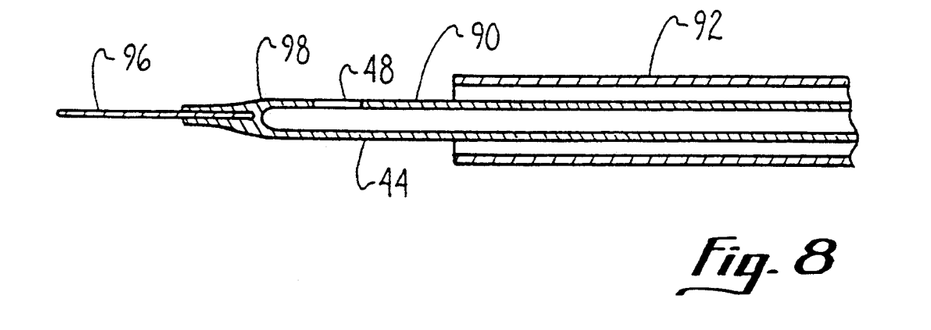
FIG. 8 is a cross-sectional view of a portion of an alternate embodiment of the catheter shown in FIG. 7 with a flexible guide member extending from the distal end of the delivery catheter.

FIG. 8 shows an alternate embodiment for the delivery catheter of the present invention in which a guide element 96 extends from the distal end 98 of a collection chamber 44. The actual attachment of the guide element 96 to distal end 98 can be accomplished by any means well-known in the pertinent art, such as by solvent bonding or heat bonding. As intended for this embodiment of the present invention, guide element 96 can be present and used in a manner well-known in the pertinent art to place the collection chamber 44 of delivery catheter 10 through the intended body passageway. As will be appreciated by the skilled artisan, the guide catheter 92 can by used to assist in the proper positioning of the collection chamber 44. Importantly, if the guide catheter 92 extends over ejection port 48 formed into the wall 90 of collection chamber 44, guide catheter 92 must be withdrawn in a proximal direction to expose the ejection port 48 before any living matter or medications can be dispensed from collection chamber 44 through ejection port 48.

Figure 9:
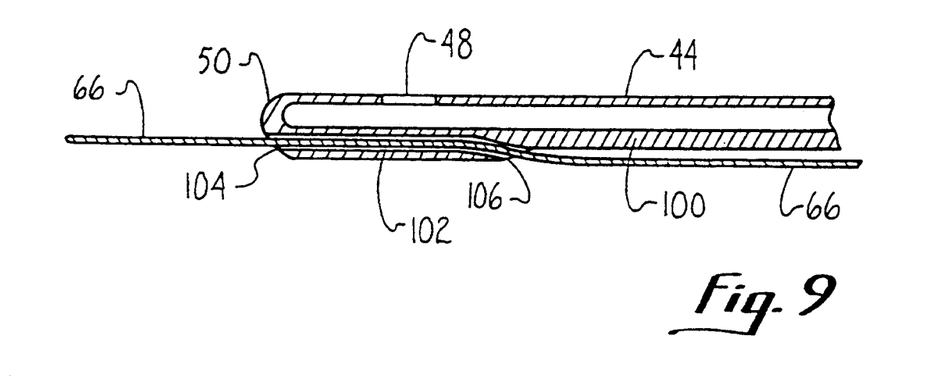
FIG. 9 is a cross-sectional view of a portion of another alternate embodiment of the present invention as would be seen along the line 3—3 in FIG. 2.

In FIG. 9, another embodiment of the present invention is shown in which the side wall 100 of collection chamber 44 is formed with a guide lumen 102. Specifically, guide lumen 102 has an opening 104 which is positioned at the distal end 50 of collection chamber 44. Also, guide lumen 102 has another opening 106 which is located proximally along the sidewall 100 from opening 104 to form a passageway through which guide wire 66 can pass. With this configuration, the guide wire 66 can be prepositioned in the particular body passageway where collection chamber 44 is to be inserted and the collection chamber 44 can receive the guide wire 66 through the guide lumen 102. Collection chamber 44 is then advanceable over guide wire 44 to position ejection port 48 of collection chamber 44 at the desired location in the body passageway.

Figures 10, 11:
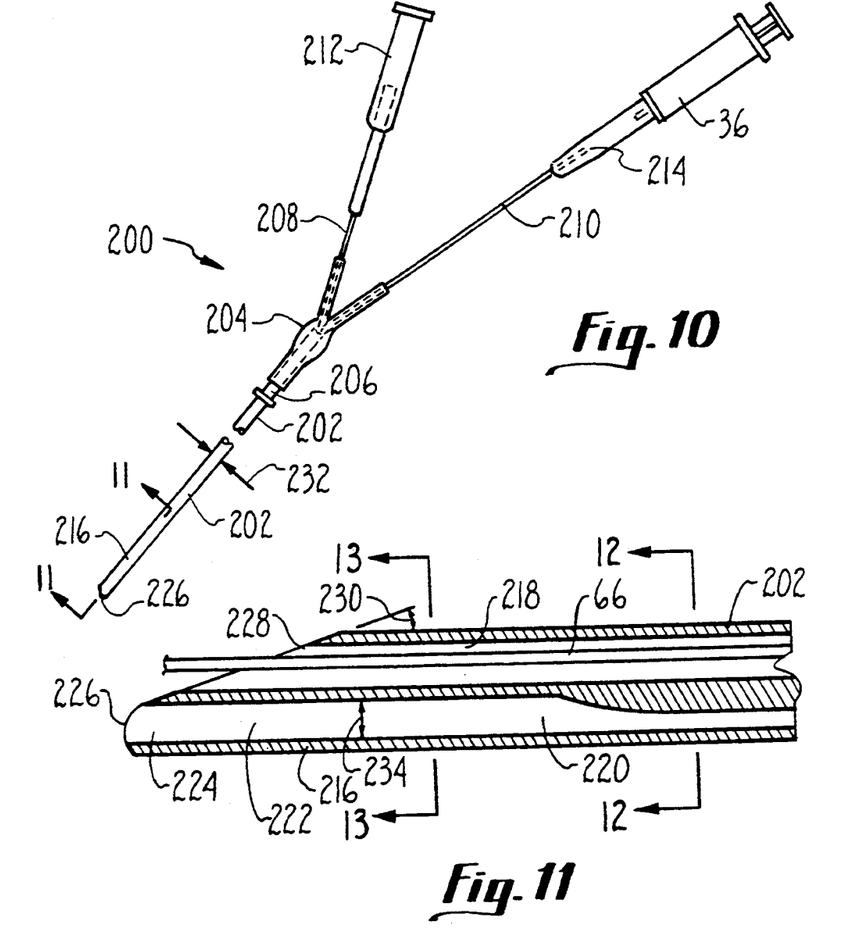
FIG. 10 is a plan view of a transfer catheter according to the present invention.
FIG. 11 is a cross sectional view of the distal end portion of the catheter as seen along the line 11—11 in FIG. 10.

Referring now to FIG. 10, another alternate embodiment for a delivery/transfer catheter in accordance with the present invention is shown and generally designated 200. As shown, the transfer catheter 200 includes an elongated, flexible, dual-lumen catheter body 202 which can be inserted into the fallopian tube 18 of a female mammal. A hub 204 at the proximal end 206 of catheter body 202 bifurcates the dual-lumen transfer catheter 200 into a guide wire branch 208 and a fluid transfer branch 210. Both the guide wire branch 208 and the fluid transfer branch 210 are each hollow tubes, and each has a respective connector 212, 214 for access into the respective branches 208 and 210.

As perhaps best appreciated by cross referencing transfer catheter 200, as shown in FIG. 10, with the cross sectional drawing of its distal end 216, as shown in FIG. 11, it will be seen that catheter body 202 is formed with a guide wire lumen 218 and a transfer lumen 220. As intended for the present invention, guide wire lumen 218 is separate from fluid transfer lumen 220 and these lumina are substantially parallel to each other. Further, guide wire lumen 218 is a continuation of hollow guide wire branch 208, and transfer lumen 220 is a continuation of hollow fluid transfer branch 210.

Figure 12:
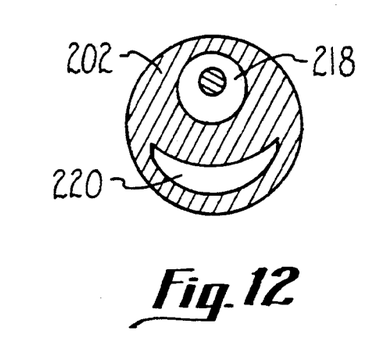
FIG. 12 is a cross sectional view of the catheter as seen along the line 12—12 in FIG. 11.
Figure 13:
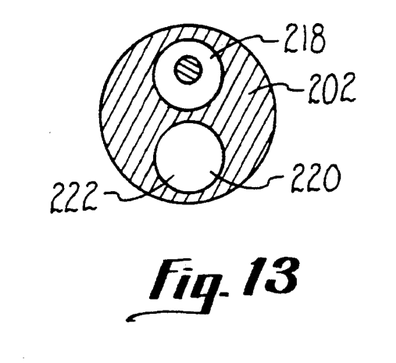
FIG. 13 is a Cross sectional view of the catheter as line 13—13 in FIG. 11.

FIG. 11 shows that a collection chamber 222 is formed at the distal end of transfer lumen 220. More specifically, collection chamber 222 is substantially cylindrical in shape and is formed with a port 224 which is located at the extreme distal tip 226 of catheter body 202. With cross reference to FIG. 12, it will be seen that the portion of transfer lumen 220 which is proximal to collection chamber 222 has a substantially crescent-shaped cross section. FIG. 13, on the other hand, shows that collection chamber 222 has a substantially circular cross section.

Referring again to FIG. 11, it will be seen that guide wire lumen 218 is formed with an opening 228 at the distal end 216 of catheter body 202. Additionally, it will be seen that opening 228 of guide wire lumen 218 is angled with respect to port 224 of collection chamber 222. The angle 230, which is a measure of the beveled relationship between opening 228 and port 224, is on the order of approximately thirty degrees (30°). Importantly, this beveled relationship between opening 228 and port 224 recesses opening 228 from port 224 with at least two beneficial results. First, with opening 228 recessed, port 224 is alone at the distal tip 226 of catheter 200. This facilitates the alignment of port 224 with matter, such as zygote 94, and makes it easier to aspirate this matter into collection chamber 222. The visual alignment of port 224 with mater to be transferred can be further facilitated by using an opaque material to make the distal end portion 216 of transfer catheter 200. Second, by recessing opening 228, the possibility that matter can be drawn into guide wire lumen 218 by unwanted capillary action is minimized.

In the manufacture of transfer catheter 200, a catheter body 202 having a guide wire lumen 218 and a transfer lumen 220 is extruded using techniques well known in the pertinent art. Initially, after catheter body 202 has been extruded, transfer lumen 220 has a substantially crescent-shaped cross section throughout the entire length of catheter body 202. A pin (not shown) is then inserted into the fluid transfer lumen 220 at the distal tip 226 of the catheter body 202. This pin is inserted into transfer lumen 220 approximately two inches (2 in.), and then withdrawn to form both the collection chamber 222 and port 224 into collection chamber 222. Hub 204 and bifurcated branches 208 and 210 can then be attached to proximal end 206 of catheter body 202 by any means well known in the pertinent art, such as by solvent bonding.

For purposes of the present invention it is intended that the outside diameter 232 of transfer catheter 200 be less than 4 French (0.053 inches). Guide wire lumen 218 must, however, still be able to accommodate an eighteen thousandths inch (0.018 in.) guide wire and the circular collection chamber 222 needs to have a diameter greater than five hundred microns.

OPERATION

In its operation, the delivery catheter 10 of the preferred embodiment is first primed with a biologically compatible fluid, such as a saline solution, and a syringe 36 is operatively engaged to the actuator port 38 of collection chamber 44. The ejection port 48 of collection chamber 44 is then placed in a container (not shown) which holds the zygotes 94 that are to be introduced into the fallopian tube 18, and the zygotes 94 are drawn into collection chamber 44 through ejection port 48 by proper operation of the syringe 36. It will be appreciated that delivery catheter 10 can also be primed with gametes insead of zygotes.

The guide wire 66 is initially inserted through a body orifice, such as the vagina of a female mammal, and is disposed with its distal end 76 positioned in the distal third portion 20 of fallopian tube 18. The guide tube 40 of delivery catheter 10 is engaged with the guide wire 66 to slidably receive guide wire 66 into the lumen 42 of the guide tube 40, and delivery catheter 10 is then advanced into position along guide wire 66. With the ejection port 48 of collection chamber 44 positioned in the distal third portion 20 of fallopian tube 18, ejection of zygotes 94 from collection chamber 44 is accomplished by introducing fluid into the collection chamber 44 through the actuator port 38. In accordance with the present invention, this introduction of fluid is accomplished by use of a syringe 36 or other fluid- injecting device.

In the operation of the alternate embodiment of the present invention, a guide catheter 72, rather than a guide wire 66, is used. For this embodiment, the priming of collection chamber 70, and the collection of zygotes 94 into collection chamber 70 is accomplished essentially as disclosed above for the preferred embodiment. Then, once guide catheter 72 is prepositioned into the body passageway, the collection chamber 70 is inserted through the lumen 74 of guide catheter 72 and advanced along guide catheter 72 until the distal end of the guide catheter 72 is positioned through the vagina and into the distal third portion 20 of fallopian tube 18. Once the ejection port 78 is positioned at the distal third portion 20 of fallopian tube 18, ejection of zygotes 94 is accomplished by introducing fluid into the collection chamber 70 through the actuator port 38 by a syringe 36 or other fluid-injecting device.

In the operation of the catheter 200 shown in FIG. 10, the distal tip 226 is positioned adjacent the matter to be transferred to the fallopian tube 18. The matter (e.g. zygote 94) is then aspirated into the collection chamber 222 through port 224. In order to insure that the gamete/zygote is not dropped during its transfer from a medium into the fallopian tube 18, it is advisable to aspirate a small air bubble into the collection chamber 222 to provide some buffer against an accidental expulsion of the matter. A guide wire 66 is prepositioned into the fallopian tube 18 and the proximal end of guide wire 66 is inserted into the guide wire lumen 218 of transfer catheter 200. Transfer catheter 200 is then advanced along guide wire 66 until distal end 216 is properly positioned in fallopian tube 18. A syringe 36 can then be activated to expel the matter from collection chamber 222 and into fallopian tube 18. Once the matter has been expelled from collection chamber 222, transfer catheter 200 is withdrawn from fallopian tube 18.

It is to be appreciated that transfer catheter 200 can be used for the transfer of several different kinds of matter. As indicated above, transfer catheter 200 is useful for depositing zygotes into a fallopian tube 18 to impregnate a female. Transfer catheter 200 may also be used to transfer biological samples to or from the fallopian tube 18, and to transfer diagnostic and therapeutic drugs directly to the fallopian tubes.

While the particular delivery catheter as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

We claim:

1. A catheter for transferring matter which comprises:
    a flexible catheter body having a distal end and a proximal end, said catheter formed with a guide wire lumen juxtaposed with a transfer lumen, said transfer lumen having a collection chamber with a port formed thereto at said distal end of said catheter body and said transfer lumen proximal to said collection chamber being substantially crescent shaped, and said guide wire lumen having an opening at said distal end of said catheter body, said opening being beveled relative to said port to effectively recess said opening of said guide wire lumen from said port of said transfer lumen; and
    means connectable at said proximal end of said transfer lumen for fluid communication therewith to draw said matter into said chamber through said port and subsequently expel said matter therefrom.

2. A catheter as recited in claim 1 wherein said port and said chamber are dimensioned to receive and hold said matter for transfer from a medium in a holding substrate to the fallopian tube of a female mammal.

3. A catheter as recited in claim 2 further comprising a guide wire, said guide wire being prepositionable to establish access to the fallopian tube and dimensioned to be received into said guide wire lumen of said catheter for advancing said catheter over said guide wire and into the fallopian tube.

4. A catheter as recited in claim 3 wherein said distal end of said flexible catheter body is made of an opaque material to facilitate visual positioning of said distal end when drawing said matter from said medium into said chamber.

5. A catheter as recited in claim 1 wherein said means connectable for fluid communications with said transfer lumen is a syringe.

6. A catheter as recited in claim 1 wherein said transfer lumen is substantially parallel to said guide wire lumen and is separate therefrom to reduce fluid friction in said transfer lumen during movement of fluid therethrough.

7. A transfer catheter which comprises:
    a guide wire prepositionable into the fallopian tube of a female mammal;
    a dual lumen catheter body having a proximal end and a distal end, said dual lumina being a guide wire lumen for receiving said guide wire therethrough and a transfer lumen substantially parallel to said guide wire lumen, said transfer lumen being formed with a collection chamber having a port at said distal end of said catheter body and said guide wire lumen being formed with a beveled opening at said distal end to recess said opening from said port; and
    means engageable in fluid communication with said transfer lumen for aspirating matter into said collection chamber and expelling said matter from said collection chamber.

8. A catheter as recited in claim 7 wherein said catheter body is flexible.

9. A catheter as recited in claim 7 wherein said matter is a gamete/zygotes and wherein said port and said chamber are dimensioned to receive and hold said gamete/zygote for transfer from a medium in a holding substrate to the fallopian tube of a female mammal and wherein said distal end of said catheter body is made of an opaque material to facilitate visual positioning of said distal end when drawing said gamete/zygote from said medium into said chamber.

10. A catheter as recited in claim 7 wherein said aspirating means is a syringe.

11. A catheter as recited in claim 7 wherein said transfer lumen proximal to said collection chamber is substantially crescent shaped and is separate from said guide wire lumen to reduce fluid friction in said transfer lumen during movement of fluid therethrough.

12. A catheter for transferring matter which comprises:
    a flexible catheter body having a distal end and a proximal end, said catheter formed with a guide wire lumen juxtaposed with a transfer lumen, said transfer lumen having a collection chamber with a port formed thereto at said distal end of said catheter body, said port and said chamber being dimensioned to receive and hold said matter for transfer from a medium in a holding substrate into a tube of a female mammal, and said guide wire lumen having an opening at said distal end of said catheter body, said opening being beveled relative to said port to effectively recess said opening of said guide wire lumen from said port of said transfer lumen;

a guide wire, said guide wire being prepositionable to establish access to said tube and dimensioned to be received into said guide wire lumen of said catheter for advancing said catheter over said guide wire and into said tube; and means connectable at said proximal end of said transfer lumen for fluid communication therewith to draw said matter into said chamber through said port and subsequently expel said matter therefrom.

* * * * *